(12) United States Patent
Cho

(10) Patent No.: US 8,578,796 B2
(45) Date of Patent: Nov. 12, 2013

(54) HIGH VOLUME SAMPLING FRONT END COLLECTION DEVICE

(75) Inventor: Inho Cho, Egg Harbor, NY (US)

(73) Assignee: U.S. Departement of Homeland Security, Washington, DC (US)

( * ) Notice: Subject to any disclaimer, the term of this patent is extended or adjusted under 35 U.S.C. 154(b) by 273 days.

(21) Appl. No.: 13/156,778

(22) Filed: Jun. 9, 2011

(65) Prior Publication Data

US 2012/0152038 A1   Jun. 21, 2012

Related U.S. Application Data

(60) Provisional application No. 61/353,866, filed on Jun. 11, 2010.

(51) Int. Cl.
*G01N 1/22* (2006.01)
*G01N 37/00* (2006.01)

(52) U.S. Cl.
USPC ............... 73/863.11; 73/28.01; 73/863.12; 73/863.21; 73/863.23

(58) Field of Classification Search
USPC .............. 73/863, 863.11, 863.12, 863.21, 73/863.23, 864.34, 28.01
See application file for complete search history.

(56) References Cited

U.S. PATENT DOCUMENTS

| | | | |
|---|---|---|---|
| 4,497,214 A * | 2/1985 | Ramelot | 73/863.12 |
| 5,345,809 A | 9/1994 | Corrigan et al. | |
| 6,470,730 B1 | 10/2002 | Chamberlain | |
| 2003/0089242 A1 * | 5/2003 | Wakamatsu et al. | 96/290 |
| 2003/0159523 A1 | 8/2003 | Renfro | |
| 2007/0034024 A1 * | 2/2007 | Syage | 73/863.12 |
| 2008/0127949 A1 * | 6/2008 | Herald et al. | 123/519 |
| 2009/0090197 A1 * | 4/2009 | Finlay et al. | 73/863.12 |
| 2009/0223310 A1 * | 9/2009 | Syage et al. | 73/863.12 |
| 2009/0320620 A1 | 12/2009 | Hu et al. | |
| 2010/0050790 A1 * | 3/2010 | Akiyama et al. | 73/863.23 |

* cited by examiner

*Primary Examiner* — Hezron E Williams
*Assistant Examiner* — David Z Huang
(74) *Attorney, Agent, or Firm* — Lavanya Ratnam; William Washington

(57) ABSTRACT

A device for sampling surfaces for the presence of compounds is provided, including a housing having a proximal end adapted to receive it negative pressure gradient and a distal end adapted to contact the surfaces; a heating element spaced from the distal end; a primary filter spaced from the heating element; and a secondary filter spaced from the primary filter, the secondary filter removably received by the housing. Also provided is as method for sampling a surface for the presence of compounds, the method including contacting the surface to dislodge the compounds from the surface; capturing first fractions of the compounds with a primary filter while allowing second fractions of the compounds to pass through the primary filter; heating the primary filter to volatilize the first fractions; capturing the volatized first fractions and the second fractions with a secondary filter; and analyzing the secondary filter to identify the compounds.

13 Claims, 11 Drawing Sheets

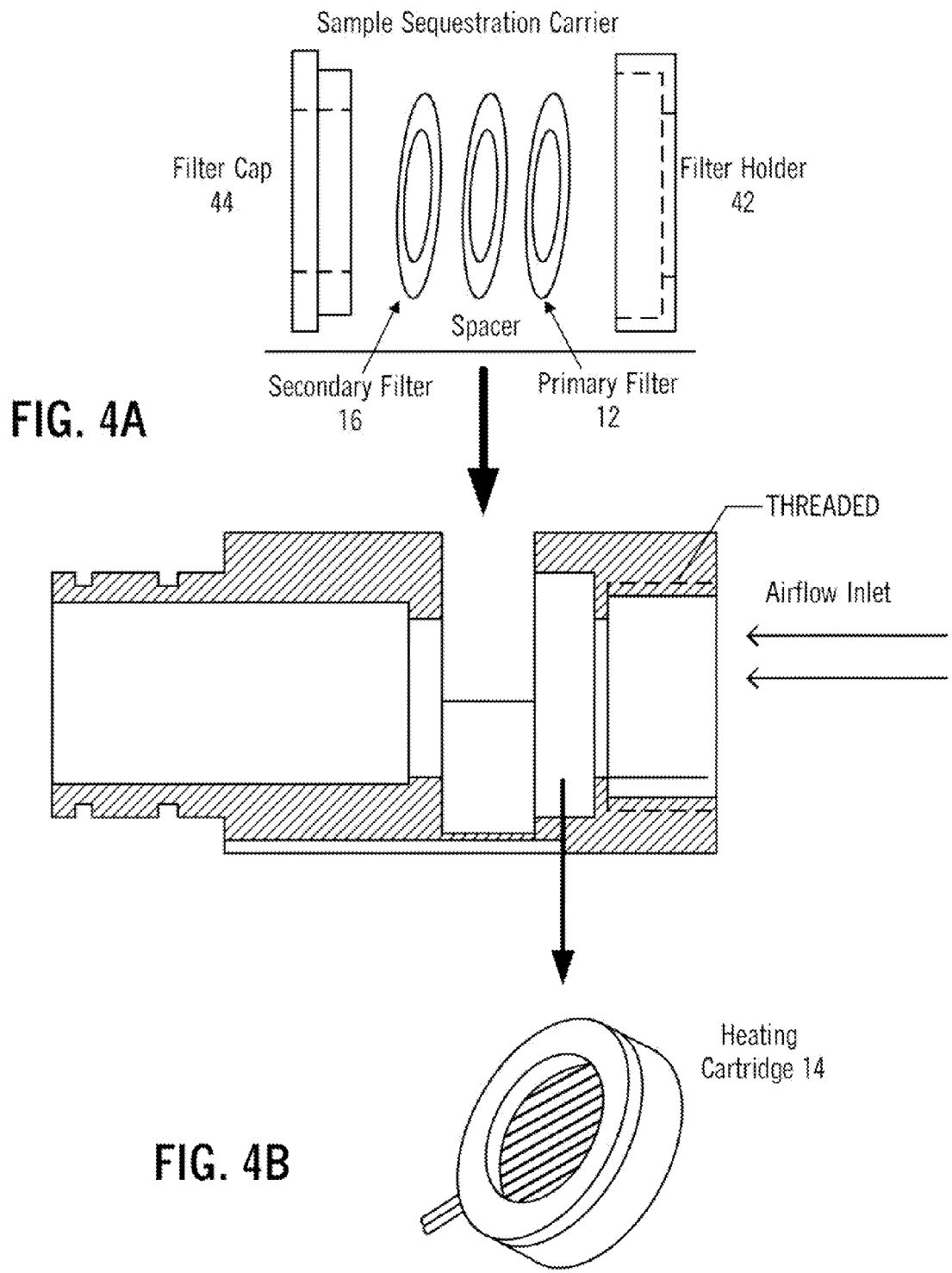

HIGH VOLUME SAMPLING FRONT END COLLECTION DEVICE

PRIORITY CLAIM

This Utility Patent Application claims the benefit of U.S. Provisional Application No. 61/353,866 filed on Jun. 11, 2010, the entirely of which is incorporated herein.

STATEMENT AS TO FEDERALLY SPONSORED RESEARCH

This invention was made with Government support under Contract N-00173-07-C-2055 funded by the U.S. Department of Homeland Security. The Government has certain rights in this invention.

BACKGROUND OF THE INVENTION

1. Field of the Invention

This invention relates to a device for high-volume sampling, and more specifically this invention is related to a particle and vapor collection device.

2. Background of the Invention

Sampling devices, specifically those used to screen large number of people or items, have been used for some time. These devices can be found almost anywhere, including government-run office buildings and airports. For example, airports use body scanners, utilizing machines that allow security officers an unobstructed view of a person's body to determine the presence of weapons. Other methods test for less visible items or substances, such as explosive residue or narcotics. Specifically, much focus has been put towards detection methods for these less visible substances as terrorism has risen, inasmuch as explosives, biochemical weapons, and the like threaten the security of the United States.

The Air Cargo/High Volume Sampling project required the development of a high volume sampling (HVS) device for testing and evaluating specifically air and sea cargo. Such cargo include goods that must be unloaded individually, typically referred to as break bulk cargo; goods transported on a skid, i.e., pelletized cargo; or containerized cargo.

Liquid preparations have been used in detection methodologies. For example, a liquid is first applied to a surface to solvate or otherwise place into liquid phase the substance of interest which may be residing on the surface. Then, that mixture is tested. While such sampling devices are reliable, they suffer from many disadvantages, one of which is efficiency. Generally, in high volume situations it would take too much time to prepare liquid samples for every surface requiring testing.

Some detection systems require encapsulating the entire object, the surfaces of which require sampling. These systems involve large chambers, and therefore require a large foot print in which to operate.

Handheld sampling wands also exist. However, many of these wands are tethered to stationary detection units, thereby hindering an operator's movement when climbing over parcels and crates.

Pretreated swabs are often used in detection protocols. Many of these sampling devices are one-offs, which is to say once they are used, they cannot be regenerated for use again. Many times the swab is destroyed by the sampling, detection process. Also, many of these devices are specific for certain target moieties, which limits their applicability to a few sampling methods.

Other detection systems include vapor deposition systems whereby adsorbents sequester vapors containing target moieties. Such systems often do not allow for simultaneous extraction and sequestration of solid phase and/or liquid phase samples.

Explosive Trace Detector (ETD) manufacturers ordinarily develop proprietary sampling technology for use in their own detection systems. Instead of retrofitting current systems and technologies, the manufactures design systems from the ground-up and require customers to replace their existing systems to obtain the new capabilities. There is no financial incentive for the manufacturers of ETDs to develop a device that can be used universally with prevalent ETDs including those from competing manufacturers.

The properties of an ideal high volume sampling device include the following:

Permits efficient and rapid collection of samples and accurate detection of substances thereon;

Adaptable to a variety of current detection and analytical machinery and systems;

Can be used for both contact and non-contact/non-invasive sampling;

Permits separation of unwanted particles from particles to be tested;

Suitable for a plurality samples including samples collected on cargo as well as those collected from passenger items, such as shoes; and Options for portability.

There is a need in the art for a detection system which is portable, light weight and low cost. The system should utilize off the shelf componentry. The system should also be capable of simultaneous sequestration of multi-phases of target compounds. And the system should allow continued sequestration of target compounds in the field by facilitating in situ replacement of full sample carriers with empty ones.

SUMMARY OF THE INVENTION

Briefly described, in an exemplary embodiment, the high volume sampling device of the present disclosure overcomes the above-mentioned disadvantages and meets the recognized need for such a device.

An object of the invention is to provide efficient and rapid collection of compounds from the surfaces of sea cargo containers, pelletized cargo, and much smaller surfaces such as shoe soles. A feature of the invention is that it is a portable device which can collect particles and vapors simultaneously on the same sample sequestration carrier. Another feature of an embodiment of the invention is that the portable device provides sample extraction and retention of target moieties for immediate analysis or delayed analysis. An advantage of the invention is that it will hold the trapped vapor compounds from an hour to a few days; the timeframe for retention of sample within the invention is dependent upon the choice of resin used within the sample sequestration carrier and chemical composition of the sample collected. An advantage of the invention is that the sample sequestration carrier is interchangeable so as to allow further sampling with the same device using unloaded carriers.

Another object of the invention is providing a portable explosive detection screening device, its portability defined as being transportable within a shirt pocket of a user. A feature of the invention is it is adapted for use with conventional vacuum systems, and analytical systems. Another feature of the invention is that the sample sequestration vehicle it utilizes can be removed from the device for analysis remotely, while not disabling the device to continue operating with another, unloaded sample sequestration vehicle. In an embodiment of the invention, airflow or sample effluent flow through the device is independent of whether its sample sequestration vehicle is in place. An advantage of this embodiment is that a first filled vehicle can be replaced with a second empty vehicle without having to interrupt flow through the system. An advantage of the invention is that its costs, weight and size relative to state of the art sampling systems are kept low due its capability of interacting with off the shelf vacuum systems, brushes, and sample ports of conventional analytic instrumentation.

Yet another object of the invention is to provide a sampling system for both contact and non-contact/non-invasive sampling. A feature of the invention is that brushes, cones or the like can be removably attached to the device by the user in the field, depending on the sampling situation encountered. An advantage of the invention is that depending on the sample tested, the device can be quickly adapted to either contact or contactless sampling, or both in the same sampling period.

Still another object of the invention is to provide a sampling system that it provides for desorption of particulate matter to release target compounds of interest. A feature of the invention is that there are two filtering stages, with the second stage physically removable from the presence of the first stage. The primary or first stage filter captures large particles that include the target compounds and unwanted dirt/dust materials. The heating element provides thermal means to desorb target compounds from material that is trapped on the primary filter. These vaporized-compounds will then be re-trapped on the secondary filter. The compounds of interest are pre-concentrated on the secondary filter for eventual analysis.

A further object of the invention is to provide a completely dry compound detection system. A feature of the invention is that it sequesters compounds of interest in a reversible adsorption process. An advantage of the invention is that the adsorbed compounds remain stable within the secondary filter for at least 10 minutes. Specific retention time will be a function of adsorbent resin and the quantity and physical properties of the trapped-compounds. Stability of the trapped-compounds within the secondary filter will facilitate transport of the secondary filter to a remote site for desorbing the sequestered compounds for identification.

Yet another option of the invention is providing a detection system with a single adsorption bed. A feature of the system is that the single adsorption bed is removable from the system. An advantage of the system is that the adsorption bed is adapted to sequester a myriad of compounds in solid, liquid and vapor phase for later analysis.

Briefly, the invention provides a device for sampling surfaces for the presence of compounds, the device comprising a housing having a proximal end adapted to receive a negative pressure gradient and a distal end adapted to contact the surfaces; a heating element spaced medially from the distal end, the heating element positioned within the housing so as to be downstream from the distal end; a primary filter spaced medially from the heating element, the primary filter encased by the housing so as to be downstream from the heating element; and a secondary filter spaced medially from the primary filter so as to be downstream from the primary filter, the secondary filter removably received by the housing.

Also provided is a method for sampling a surface for the presence of compounds, the method comprising contacting the surface for a time and with a pressure to dislodge the compounds from the surface; capturing first fractions of the compounds with a primary filter while allowing second fractions of the compounds to pass through the primary filter; heating the primary filter for a time and at a temperature sufficient to volatilize the first fractions; capturing the volatized first fractions and the second fractions with a secondary filter; and analyzing the secondary filter for the identity of the compounds.

These and other features and advantages of the high volume sampling device of the present disclosure will become more apparent to those ordinarily skilled in the art after reading the following Detailed Description of the Invention and claims in light of the accompanying drawing figures.

BRIEF DESCRIPTION OF THE DRAWINGS

The invention together with the above and other objects and advantages will be best understood from the following detailed description of the preferred embodiment of the invention shown in the accompanying drawings, wherein

FIG. 4 is a perspective view of a heating element far use with the embodiment depicted in FIG. 2;

FIG. 5 is a perspective view of an embodiment of the device, in accordance with a cup brush attachment.

DETAILED DESCRIPTION OF THE INVENTION

Figure 1:
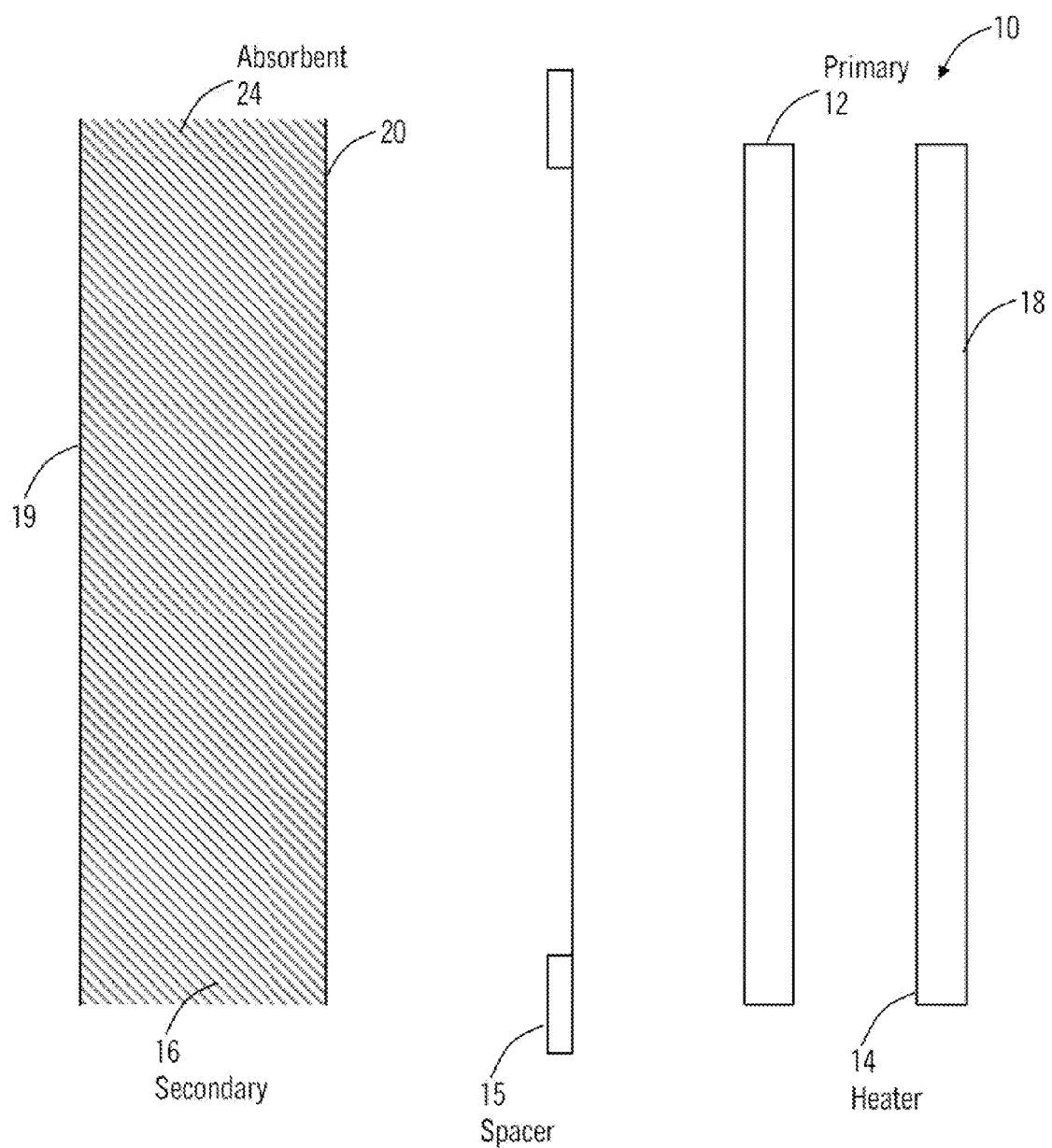
FIG. 1 is a schematic of an explosive trace collection device, in accordance with features of the present invention.

In describing exemplary embodiments of the high volume sampling device of the present disclosure illustrated in the drawings, specific terminology is employed for the sake of clarity. The claimed invention, however, is not intended to be limited to the specific terminology so selected, and it is to be understood that each specific element includes all technical equivalents that operate in a similar manner to The invention provides a front end specimen collection device for use in detecting trace quantities of explosives, pathogens, and other target compounds accomplish a similar purpose in high volume throughput scenarios. The device is adaptable for use with typical detection equipment and analyzers. Sampling rates of the commercial vapor detectors are 1 to 4 Liters per minute in approximately ¼" ID sample inlet. However, the HVS sampling rates are between about 40 to 400 Liters per minute thru a 1" ID sampling port. The sample flow rates are a function of the power of the vacuum pump which facilitates sample routing through the invented device. Throughput limits depend on an application of the sampling device, with some applications requiring a large volume of the air samples from the target area. For example, the palletized-cargo, the containerized cargo (20' to 40' sea containers), or vehicle born improvised explosive device (VBIED) applications require a large volume of the air sample. However, the TSA checked bag screening, the TSA checkpoint passenger screening, or PBIED (Person Borne IED) application requires a small volume of sample.

In large volume sampling, the device is adapted to be in fluid communication with a ventilation port of a cargo container, such that for example the device is placed upstream or downstream of the ventilation port, or perhaps within and coaxial to the port. In small volume sampling, an upstream end of the sample collection device terminates in a means for physically brushing, scraping or otherwise contacting target surfaces while a negative pressure is applied to a downstream end of the device. Such physical contacting means includes an oscillating brush, Generally, the front end collection device comprises a heating cartridge, a sample primary collector and secondary collector positioned downstream of the primary collector. The secondary filter may include one of several polymer adsorbents to trap vapor samples. The heating cartridge and collectors are supported by a housing so as to be substantially encased by the housing. The shape of the housing can be variable, depending on its use. As depicted in the figures, the housing is cylindrical so as to allow for easy manipulation by a single hand of a user.

The primary filter captures most of the large particles that includes the target compounds and unwanted dirt/dust materials. And then the primary filter is heated at ~350° C. to evaporate the compounds that trapped on the primary filter. The vaporized-compounds will be re-trapped on the secondary pre-concentrator (or Tea-bag). During the process, about 1 to 4 L/min of flow will be applied to the device for carrying target moieties through the device.

The term front end collection device refers to the typical protocol of using the device to collect a sample before that sample is analyzed via wet bench processes, solid state desorber systems, or combinations thereof. It is designed to be used with conventional detection systems/processes, and reused after those analysis processes desorb the target compounds from the secondary collector of the device.

In an exemplary embodiment of the invention, an aluminum housing holds the primary and secondary concentrator, with a Teflon ring separator positioned between the two concentrators. The heating cartridge is positioned in the front of the primary filter, and is generally activated after sample collection. The main function of the primary filter will be to collect large particles, dirt, dust, and analyte particles. The secondary concentrator, comprised of Tenax (polymer adsorbent material) collects vapors and analytes from the primary filter after that primary filter is heated up to about 300° C. within about 10 seconds, and then vaporize some of the particles and analytes collected from the primary filter.

A schematic of an exemplary high volume sampling (HVS) device sample capture area is depicted as numeral 10 in FIG. 1. High volume sampling encompasses sample volumes as high as approximately 400 liters per minute of air using a 1 inch inner diameter input aperture such as a 1" ID sample tube combined with a cup brush. (Higher sample volumes are attainable if input diameters increase.) Viewing the figure from right to left, the device is comprised of distinct subunits, including but not limited to a means 14 for heating, a first filter 12, and second filter 16 or pre-concentrator. Either a distal end 18 of the device 10 is adapted to receive pressurized effluent (not shown), or a proximal end 19 of the device is adapted to establish fluid communication with negative pressure (i.e., a vacuum pull, also not shown). In an embodiment of the device, a vacuum pull is established between the proximal end and a vacuum line via a snap fit assembly or threaded connectors.

Figure 2A:
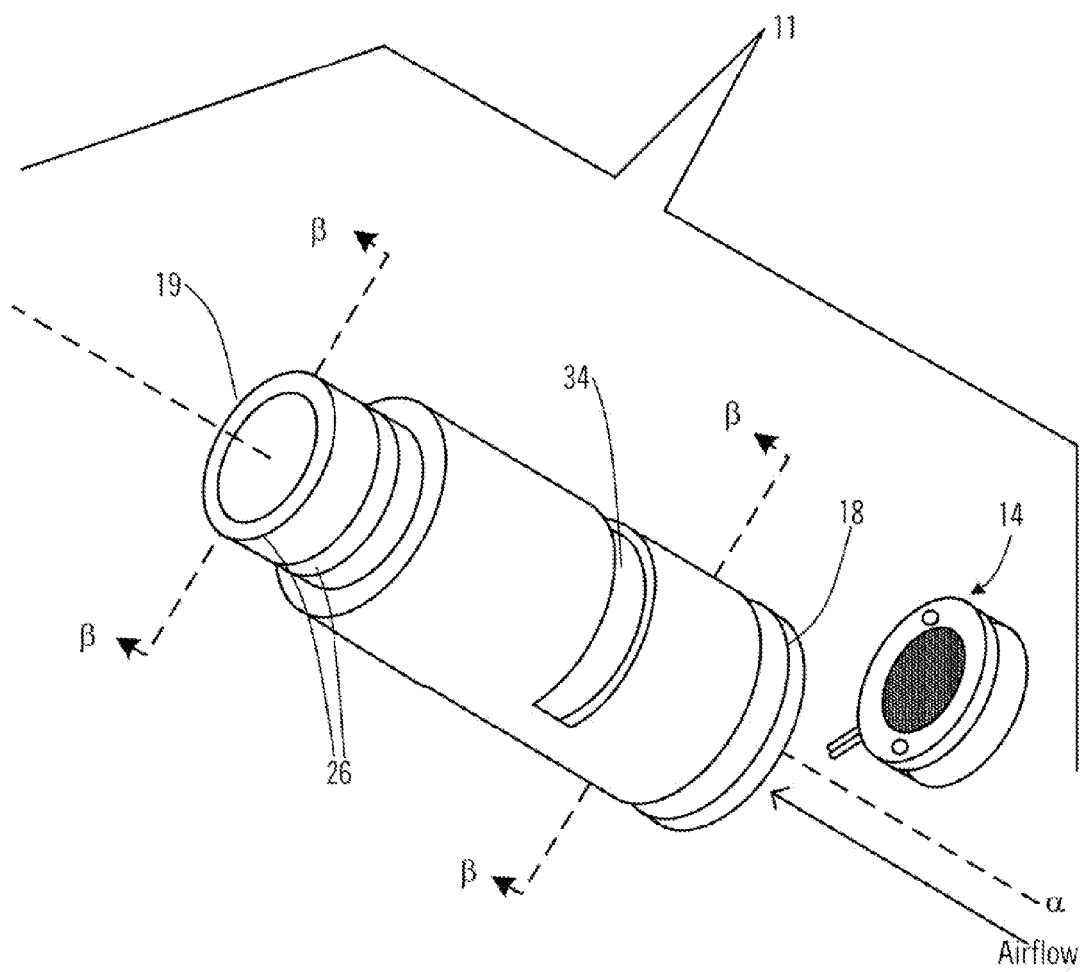
FIG. 2 is a perspective view of an embodiment of an explosive trace collection device, in accordance with features of the present invention.
Figure 2B:
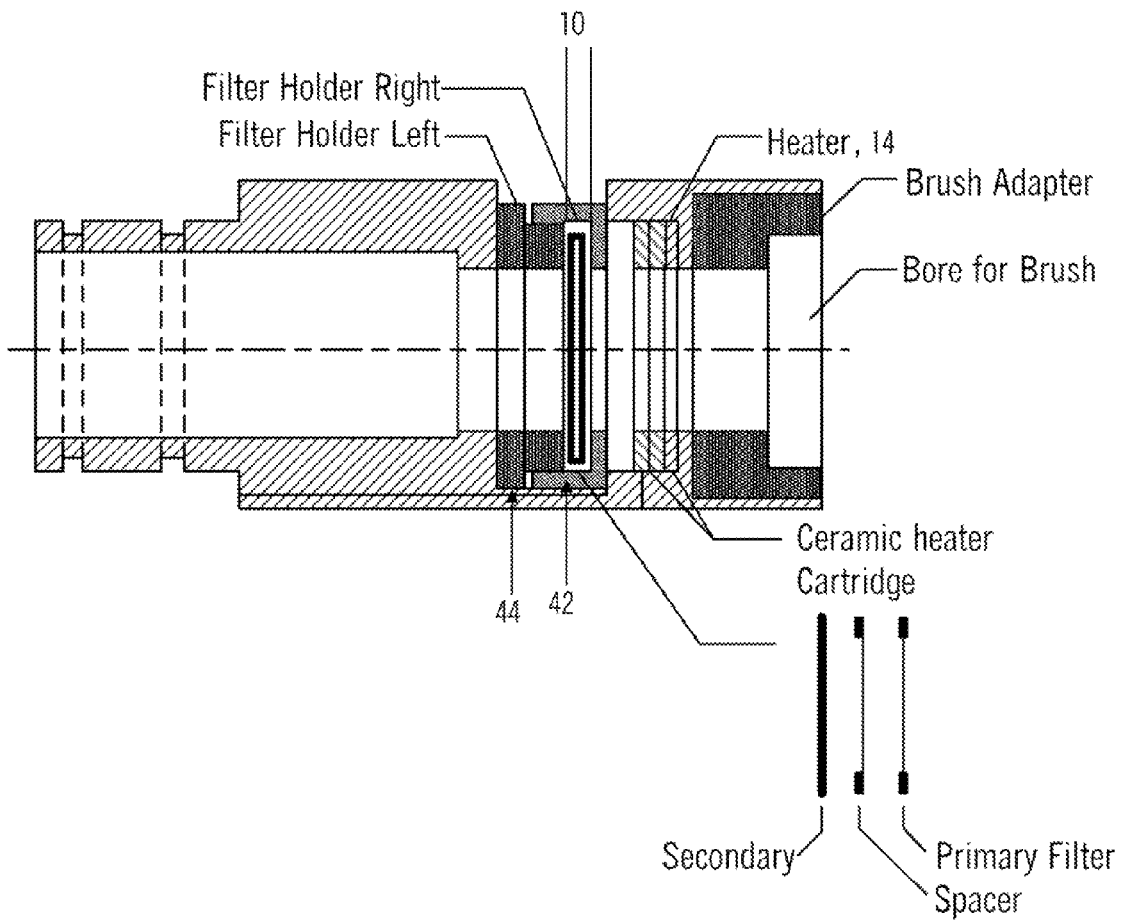
Figure 2C:
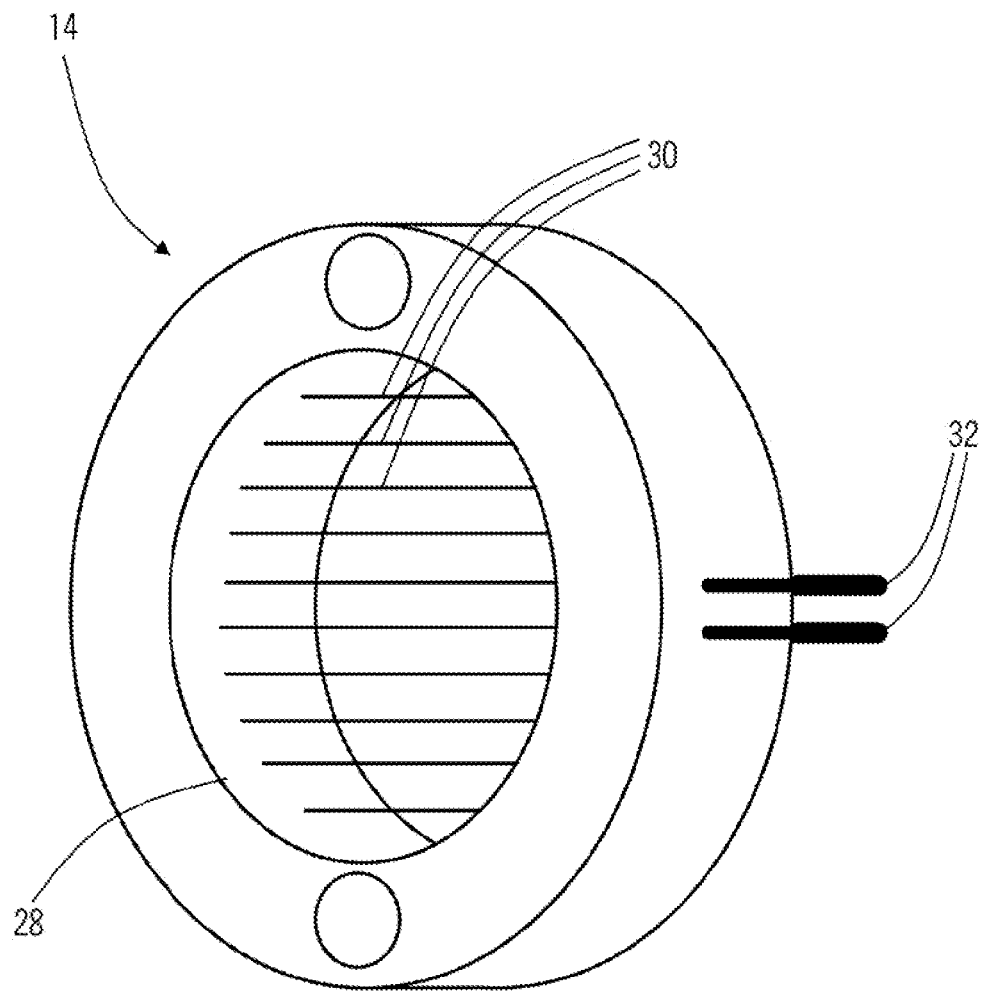

FIG. 2 is a perspective view of an embodiment of the invented HVS device. The proximal end 19 of a housing 11 of the device defines annular grooves adapted to receive o-rings 26 or other sealing means to effectuate a negative pressure pull with a vacuum hose (not shown). As noted supra, this housing 11 is depicted as cylindrical in shape, but other shapes are also envisioned. For example, the cross sections of exemplary housings 11 may be complementary to ventilation shafts or conduits of large cargo bays.

Figure 3A:
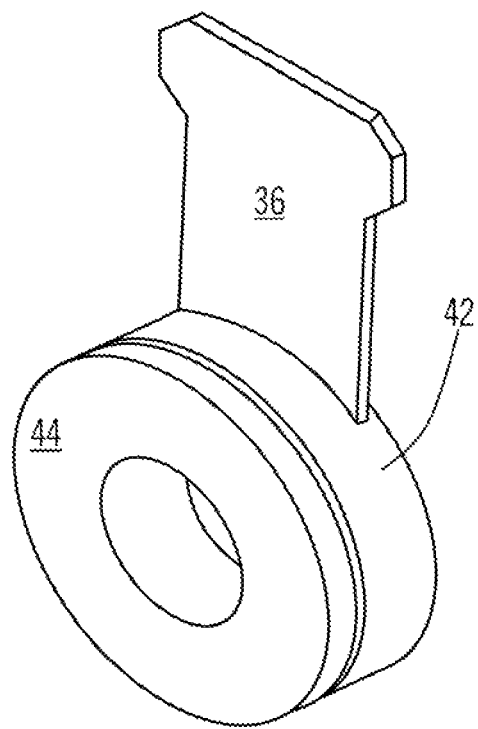
FIG. 3 is a view of FIG. 2 taken along lines B-B.
Figure 3B:
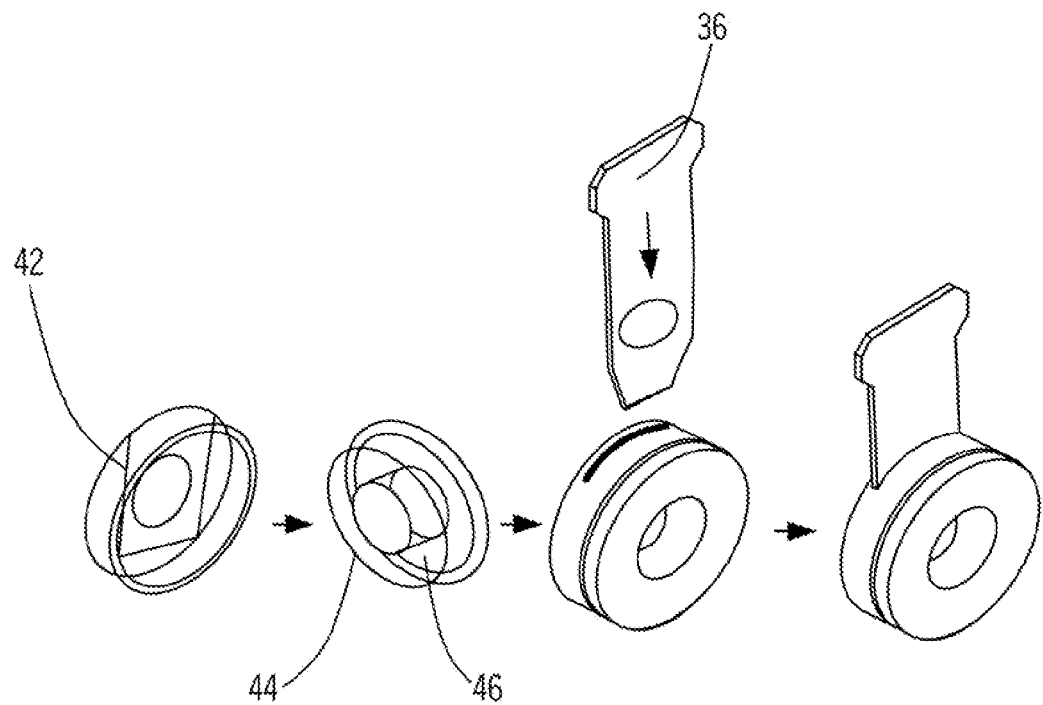
Figure 5:
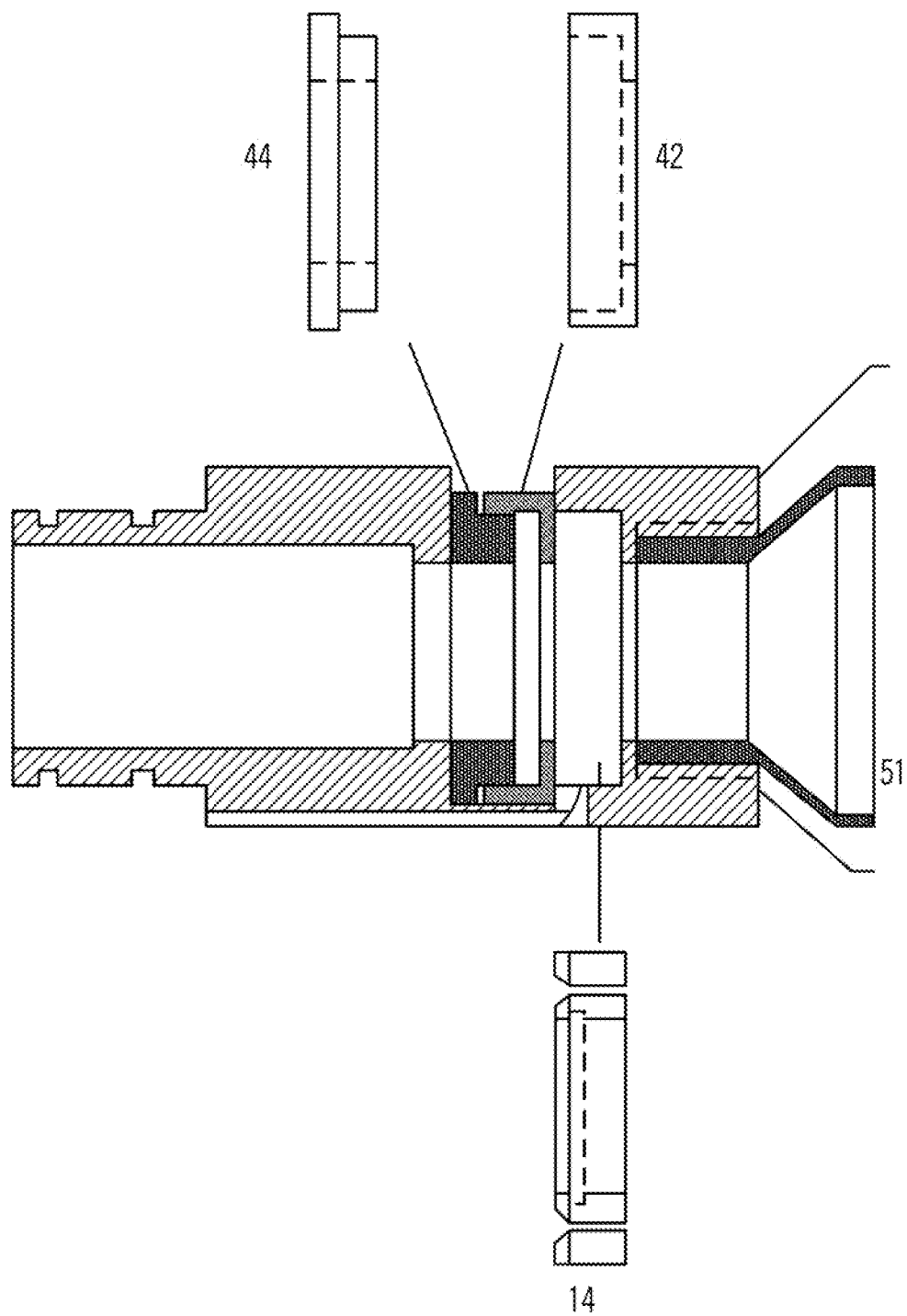
FIG. 5 is a perspective view of a sample sequestration vehicle containing the apparatus of the secondary filter, for use in an explosive trace detection device, in accordance with features of an embodiment of the present invention; and adapted for use in a Morpho Detection ETD system.
Figure 6:
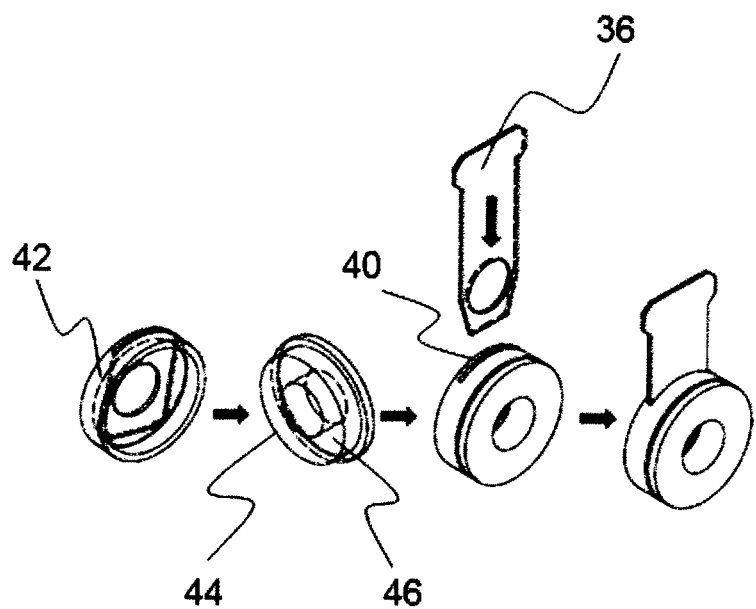
FIG. 6 is an exploded view of the sample sequestration vehicle housing forming the removable portion containing the secondary filter adapted for use by the Morpho Detection ETD system.
Figure 7:
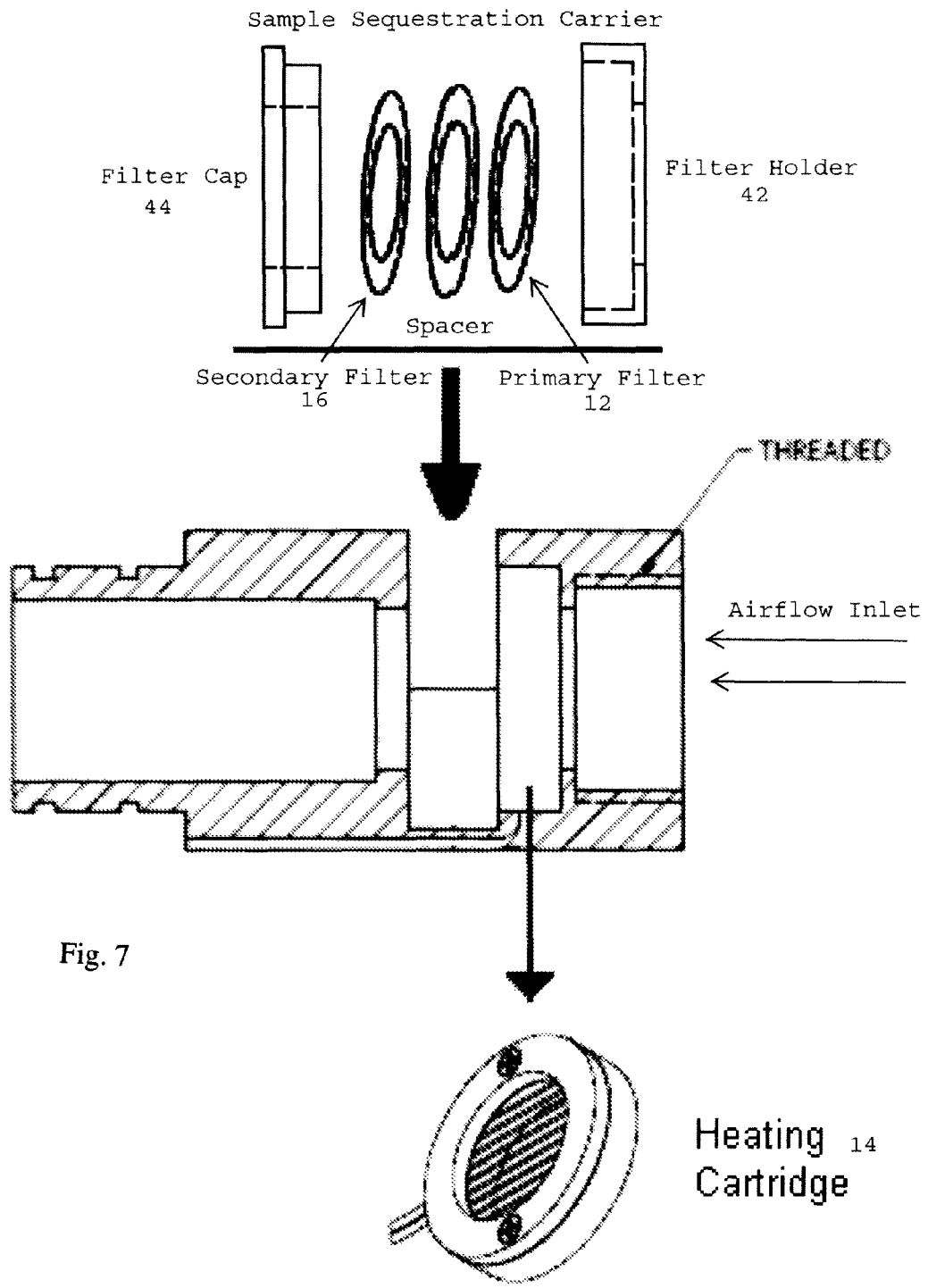
FIG. 7 is a perspective view of an embodiment of the device, in accordance with features of the removable sample sequestration carrier housing forming the secondary concentrator.

FIG. 3 is a view of FIG. 2 along lines B-B. This embodiment of the invention differs from the schematic depicted in FIG. 1 in that the primary 12 and secondary 16 filters are shown contained within the apparatus housing 11. In an alternative embodiment the primary and secondary filters could be contained within a single sample sequestration vehicle 16 such that when the vehicle is removed, both primary and secondary filters are removed together and therefore simultaneously from an aperture 34 within the housing 11.

A distal end or upstream end 18 of the device is adapted to receive, and optionally encapsulate the heater module 14, the module depicted in greater detail in FIG. 4

The HVS frontend device can be attached to a commercial vacuum system with some modifications. Currently, two commercial vacuum systems have been tested: (1) the Dayton Backpack Vacuum system (Model4TRI0) and (2) the Dyson handheld vacuum system (Model DCI6). The HVS Frontend device was designed to adapt to both systems, and collection activities lasted anywhere from several seconds to several minutes.

Figure 8:
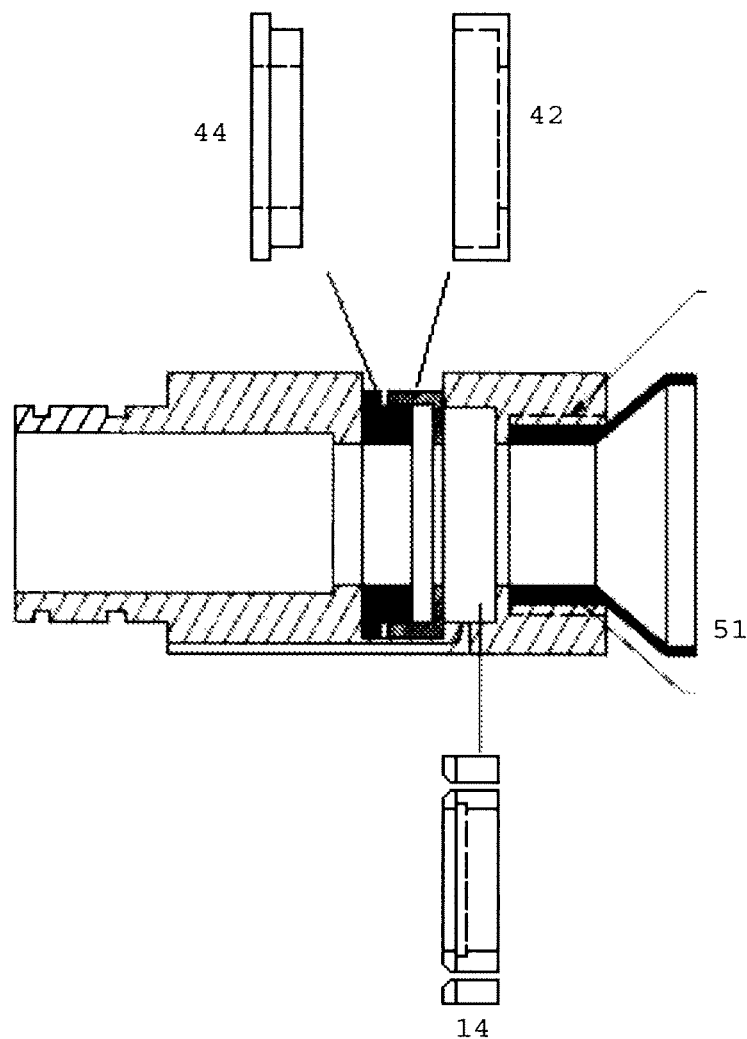
FIG. 8 is an exploded view of an embodiment of the removable sample sequestration carrier.

The HVS frontend device can be applied in two sampling techniques: (1) a contact and (2) a noncontact sampling method. The contact sampling method, embodied in FIG. 8, uses a cup-shaped brush that is attached to the front of the device to remove the dirt, dust, and particles of interest from the test substrate, in an embodiment of the invention a negative pressure exists during the contact technique such that moieties dislodged from surfaces to be scrutinized are continually being directed to the primary and secondary filters.

The noncontact sampling technique utilizes the device without any physical contact and collects airborne particles and vapor samples.

Primary Filter Detail

Sampling always collects some degree of unwanted particles along with the target compound. A main function of the primary filter is to collect large particles, such as dirt, dust and analyte particles during its initial contact with the suspected surface. Therefore, the device has a primary filter to collect large particles from the sample. Any relatively inert or nonreactive material (relative to the target compounds being sought) is suitable as a primary filter. This inert or nonreactive material also preferably withstands temperatures of at least between about 250° C. and 500° C., and most preferably between 300° C. and 350° C.

An embodiment of the invention utilizes stainless steel mesh as a constituent of the primary filter. The primary filter is made of between about 200 mesh and 400 mesh stainless steel screen, and can be heated to 350° C. to vaporize materials on its surface. The primary filtration desorption process occurs within about 20 seconds, preferably between about 5 and 15 seconds, and most preferably between 5 and 10 seconds. The desorption is accompanied with an airflow through the device so as to direct desorbed moieties from the primary filter 12 to the secondary filter. Exemplary flow rates range from between approximately 250 and 1500 cc/minute, and preferably between 500 and 1000 cc/minute.

The vaporized samples are collected on the secondary filer situated downstream of the primary filter. The sample sequestration vehicle containing the secondary filter is then removed from the device after which the secondary filter is placed directly in an explosive trace detection system. This design provides a means for sampling both solids and fluids simultaneously.

Secondary-Filter Detail

The secondary filter collects vapor and/or particle samples and can be directly inserted into conventional detection instrumentation such as the Smiths Detection 500DT (Morristown, N.J.) or the Morpho-Detection ETD Systems (Wilmington, Del.). However, the secondary filter is adaptable to also fit sample insert ports of other desorption/detection devices.

The secondary filter is adapted to be removably received by the housing 11 of the device. FIG. 5 is a perspective view of the secondary concentrator 16 and FIG. 6 is an exploded view of the secondary concentrator. The secondary concentrator comprises a housing which is donut shaped so as to be slidably received by a complementary aperture 34 formed along a longitudinally extending surface of the housing 11 of the device. In the embodiment shown, the aperture defines a plane which is positioned transverse to the longitudinal axis of the device 10. In an embodiment of the invention the secondary filter 16 is adapted to fit the sample input shape for a Smiths Detection EDS system. The Smiths Detection EDS system utilizes a round sample input shape and the secondary filter 16 in this embodiment is of a corresponding shape that is contained entirely within the sample sequestration vehicle.

As depicted in FIG. 6, the housing of the sample sequestration vehicle further comprises a base 42 and a cap 44 matingly received by the base so as to form an interior space 46. The interior space is adapted to receive the secondary filter material, comprising adsorbent. In an embodiment of the device, the base 42 has a depth measuring at least the thicknesses of the primary and secondary filters combined.

As depicted in FIG. 7, the sample sequestration vehicle is doughnut shaped (i.e., the shape of a disk) and substantially completely encases the secondary filter 16. The secondary filter 16 is adapted to fit the sample input port of a Smiths Detection EDS system. The Smiths Detection EDS system utilizes a round sample input shape and the secondary filter 16 in this embodiment is of a corresponding shape that is contained entirely within the sample sequestration vehicle.

The sample sequestration vehicle may be circular or of alternative shape to fit the parameters of the sample input region of the detection instrument used to analyze the secondary filter. For example, FIG. 6 depicts a carrier 36 for a secondary filter whereby the carrier mimics the size and shape of sampling swabs accepted by some state of the art detectors. One such state of the art detector is the Morpho Detection EDS system. This carrier 36 comprises a flat substrate which laterally extends from the concentrator so as to be coplanar with the plane formed by the cross section of the housing of the sample sequestration vehicle. The substrate 36 is matingly received by a peripheral region of the base 42 forming a slot. Once received by the slot, the substrate 36 is finally positioned near the downstream end of the sample sequestration vehicle as the secondary filter. This substrate comprises a first end 37 which allows a user to manipulate it (i.e., insert it and remove it from the sampling device and insert it and remove it from a detector). The substrate 36 further comprises a second end 39 which comprises secondary filter material.

The secondary-filter is capable of collecting vapor and micrometer-sized particles simultaneously. The mesh size of the primary filter 12 will determine the size of particles captured in the secondary concentrator 16. For example, given a primary mesh size of 74 microns, particles smaller than that will be sequestered by the secondary concentrator.

After samples are collected on the secondary-filter, the secondary-filter is separated from the device and the sample sequestration vehicle and placed directly in whatever state of the art trace detection systems being used.

In an embodiment of the invention, the secondary-concentrator 16 defines a planar configuration with a fiberglass filter mesh 20 defining an upstream side surface and a stainless steel mesh defining 19 a downstream side surface. Intermediate the fiberglass filter and stainless steel mesh is an adsorbent 24 such as porous polymer resin. A class of exemplary resins comprise diphenylene-oxide on a heat resistant substrate such as graphite. Tenax-GR, available through Scientific Instrument Services of Ringoes, N.J. commercially supplies such a resin. Other suitable resins include Supelco (Sigma-Aldrich), Restek, Perkin-Elmer, Agilent, and combinations thereof.

An embodiment of the sorbent entity 24 comprises 200 mesh (approximately 74 microns) stainless steel with between 75 and 200 milligrams of Tenax-GR backed therein. The trap materials (i.e., resin) are placed in between the two stainless steel wire cloth or fiberglass substrates, then, a tap welding machine is utilized to weld the edges of the cloth together, thereby substantially encapsulating the trap materials within the wire cloth. Generally, when Tenax-GR resin is utilized, its mesh size is between 80 and 100 or particle sizes having diameters of between about 180 microns and 145 microns.

When Tenax TA resin is used, its mesh size is between about 60 and 80.

Alternative embodiments of the secondary filter 16 include stainless steel mesh on the upstream and downstream side; or adsorbent treated fiberglass mesh on the upstream side that is sown, heat welded or otherwise mated with a stainless steel mesh on the downstream side. Inasmuch as the desorption temperature is a flash heating at approximately 350° C. for a few seconds, material such as fiberglass positioned proximal to the desorption process (i.e., positioned adjacent the heated primary filter) is not in danger of melting or otherwise decomposing. Generally material so proximally arranged which have melting or decomposition temperatures above 350 C are suitable. For example, fiberglass can withstand temperatures well above 400° C.

A specific embodiment of the secondary filter 16 is stainless steel 200 mesh. Particle sizes of the adsorbent resin are 150 to 250 μm. The invention can accommodate a mesh portion of the secondary filter composed of alternative materials that are inert or non-reactive with the target compounds. For any applicable secondary filter, in order to accommodate the adsorbent resin particles, the stainless steel mesh is preferably smaller than adsorbent particles.

Fiberglass filter is suitable for use in the particle collection systems. Suitable fiberglass filter is commercially available from Smiths Detection and TeknoScan (Vaughan, Ontario, Canada). In an embodiment, the secondary filter is fabricated with a 0.02" thick fiberglass filter along with a 200 mesh stainless steel cloth wire. The combination is suitable for about 60-100 mesh Tenax adsorbent resin particle sizes. Optionally, the fiberglass is treated with graphite. Graphite or other material with hydrophobic properties that will prevent accumulation of moisture on the secondary filter.

Heater Detail

A salient feature of the device is that it sequesters solid and gaseous phase moieties. At the start of sampling, gas phase moieties pass through the first filter 12 and are collected by the resin in the secondary filter 16. Simultaneously, particulate matter collects on the primary filter. A heating cartridge 14, positioned upstream of the primary filter 16, is then activated.

After the heater is activated, negative pressure is applied to the downstream end of the device. The adsorbent resin in the secondary filter collects vapor which is generated when particulate on the primary filter vaporizes As such, the heating means increases the temperature of the primary filter up to about 300° C. and within 10 seconds. This causes some of the particles on the primary filter to be vaporized for adsorption by the secondary filter downstream.

Detail of an exemplary heating cartridge is found in FIG. 4. The module is seen as ring-shaped. When positioned on the device, the center of a primary opening 28 of the module is coaxial with the longitudinal axis a of the device 10. A plurality of heating coils 30 extend traversely across the opening, those coils energized by electrodes arranged along a laterally facing periphery of the module. In an exemplary embodiment of the heating cartridge, the housing defining the module is comprised of metal, ceramic, high temperature resistant polymer, or combinations thereof. The housing can be homogeneous in construction in that it comprises solely one material throughout, or the housing can be heterogeneous in construction. The coils comprise a nichrome alloy wire with a thermal conductivity of between approximately 10 and Wm-1° C.-1 and a gauge size of between approximately 20 and 24. An exemplary wire for heating element purposes for an embodiment of the invention is 24 G N6 alloy wire, having a resistance of about 1.7 Ohms/ft.

The heating module is seen as being reversibly attached to the device 10. However, a module integrally molded to the housing 11 of the device is another option.

In an embodiment of the invention, the heater is activated when negative pressure is applied to the device, such as the connection of a vacuum tube. As such an electrical switch is located on a front end of the vacuum hose. Alternatively, the heater may be activated prior to the sample collection, or after sample collection if suction is applied so that collected particles vaporized on the primary filter are transported to the pre-concentrator.

The heating element can be heated up to approximately 450° C. A suitable heating range is from about 300° C. and 450° C., with a preferable temperature of about 350° C. The aforementioned temperatures are optimized using 24 gauge Nichrome® wire comprising the heating module wire grid. Temperatures at least about 250° C. may be used to desorb material collected on the primary filter by using additional or alternative heating elements.

Once the primary filter is heated and analyte is collected in the secondary filter (i.e., pre-concentrator), the secondary filter can be then analyzed by sliding it into the desorption tray of the Smiths Ionscan 400B. Alternatively, analysis by a Smiths Ionscan 500DT has been achieved by modifying its sampling wand to accommodate the pre-concentrator. The wand slides into the 500DT desorber just as does a regular swab sample.

After the adsorbed compounds are thermally extracted from the adsorbent resin (through analysis by the detector), the resin within the secondary filter is reusable for the next sample taking. A salient feature of the invention is that aside from desorption processes occurring within the detector, no separate regeneration or reconditioning of the secondary filter or its components is necessary between sample taking. In an embodiment of the invention, to assure longevity of the secondary filter and the polymer encapsulated therein, a means for isolating the secondary filter from the heating module is provided. One such means is a disk-shaped spacer 15 positioned between the primary filter 12 and the secondary filter 16. Constituents of the spacer can be any thermally insulating substance, including, but not limited to plastic, Teflon, ceramics, or other inert materials that are thermally insulating, and combinations thereof.

In an embodiment of the invention, a polytetrafluoroethylene, ring-shaped spacer, such as Teflon ring, is utilized to prevent direct contact between the primary filter and the secondary filter.

The separator should prevent direct contact each component, but also preferably should be short enough to prevent condensation between the primary filter and pre-concentrator.

In operation, the High Volume Sampling device can be applied to the break bulk, pelletized or containerized air/sea cargo. Also, the device can be utilized on chemical and biological warfare agent samples, industrial toxic chemicals, explosives particle samples, and drugs or hazardous waste sampling. The HVS device facilitates large volume of air sample collection from a large screening area.

The military explosive, Composition C-4, was used as a standard explosive for the device particle sample testing. In the contact sampling processes, the device collection limit ranged from 25 ng to 50 ng per sample. Table 1 provides detection results of the invented device for various target materials.

TABLE 1

Qualitative Results on Smith Detection Ionscan 400 B ETD

| Deposit Mass | Cardboard | Plywood | Shoe | Vapor Sample |
| --- | --- | --- | --- | --- |
| C-4, 25 ng | 60% | 60% | 80% | |
| C-4, 50 ng | 100% | 100% | 80% | |
| TATP[1], 250 mg | | | | |
| EGDN[2], 450 mg | | | | 100% |

[1]Triacetone triperoxide.
[2]Ethylene glycol dinitrate

In Table 1, the cardboard represents bulk cargo, the plywood represents cargo freight and the shoe represents shoe PBIED (Person borne improvised explosive devices.). The aforementioned contact particle technique was used to collect samples from these various surfaces. A known quantity of the compound was first deposited on each of the surfaces using a dry-transfer technique, one exemplary technique disclosed in U.S. Pat. No. 6,470,730, incorporated herein by reference.

Then, a brush agitator was used to remove particles from the test articles. This brush agitator is positioned at the distal end of the collection device (via a male-female threaded interaction, or a snap fit coupling means). Brush sizes will depend on the intake orifice of the device. A myriad of brushes are commercially available. For example, Carolina Brush of Gastonia, N.C., manufactures cup brushes 1.17" OD and 1.875" OD.

The proximal end of the device is maintained at negative pressure so as to provide a means for directing particles, loosened by the agitator, through the device. Flow rate through the device varies from between about 50 to 100 liters per minute and preferably about 90 liters per minute.

Vapor-phase samples were collected using the invented device wherein its distal end instead terminates in a frusto-conically shaped tip. In an embodiment of the device, a cone comprised of inert, nonstick material (such as Teflon®) and having approximately a 1.5 inch wide mouth is attached to the distal end (i.e., the front end) of the device. The cone shape provides a means to direct target organic vapor sample through the filters encapsulated by the housing of the device. Some of the target analytes in explosive vapor sampling include high volatile organic compounds (MNT, NG, EGDN, and DMNB (taggent).

As identified above, the HVS frontend device can be used for both contact and noncontact sampling. Also, the sample analysis can be performed using existing prevalent explosive trade detection systems. The device retrofits the sampling methods of existing trace detection systems of various manufactures for the detection of sample collected via noncontact sampling.

The device is designed to be portable or stationary.

In operation, an embodiment of the device is first subjected to a negative pressure pull, for example, via a suction hose removably attached to the proximal end of the device. The distal end of the device is physically contacted to a surface suspected of contamination. This first step simultaneously removes any particulate and gaseous moieties from the surface, the particulate moieties to be stopped by the primary filter and the gaseous moieties to pass through the primary filter and stopped by the secondary filter.

The operator then powers up the heater. The higher temperature vaporizes any particulate captured on the primary filter. The rising temperature also causes any high vapor pressure contaminants on the surface to volatilize and be drawn through the primary concentrator and adsorbed to the secondary concentrator. Simultaneously, a scrub brush, or any other abrasive substrate positioned at the end of the distal end of the device, dislodges solid and liquid phase contaminant from the surface, to also be passed through the primary filter and sequestered in the secondary filter.

The sample sequestration vehicle is then separated from the housing of the device, the secondary filter is removed from the sequestration vehicle and inserted into a desorption/detection instrument, subjected to wet bench analysis, or both. This desorption step serves also as a regeneration step for the secondary filter. As such, the secondary concentrator is subsequently reinserted into the sample sequestration vehicle, the vehicle reinserted into the housing of the device, and the device is ready for another round of sample taking.

Sampling times are based on the specific sample environment. For TSL applications, 30 second sampling time is suitable for particle collections and 60 seconds for vapor collections.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting, but are instead exemplary embodiments.

The device is designed to be portable but an alternative embodiment should be able to collect sample from large/infinite areas by acceleration of the airflow through the device (enlarging the vacuum and/or the interior diameter of the secondary filter) and variation in the density of the absorbent resin contained within the secondary filter. The device is not limited in sample collection ability by volume of the screening area, but limitations may be expressed upon the utility of the device only by the empirical constraints of the chemical analysis unit and its ability to analyze the pre-concentrator. Specifically, minimum detection limits will be a function of absorber resin and chemical detector limitations.

Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

The invention claimed is:

1. A device for sampling surfaces for the presence of compounds, the device comprising:
   a. a housing having a proximal end adapted to receive a negative pressure gradient and a distal end adapted to contact the surfaces;
   b. a heating element spaced from the distal end, said heating element positioned within the housing;
   c. a primary filter spaced from the heating element, said primary filter encased by the housing; and
   d. a secondary filter spaced from the primary filter, said secondary filter removably received by the housing;
   wherein, when the heating element heats the primary filter, particles collected by the primary filter are vaporized, and the vaporized particles are collected by the secondary filter for analysis thereof.

2. The device as recited in claim 1 wherein the distal end defines an opening of the housing and is adapted to receive a brush which engages substantially the entire periphery of the opening.

3. The device as recited in claim 1 wherein the distal end defines an opening of the housing and is adapted to receive a frusto-conically shaped sleeve to engage with the surface.

4. The device as recited in claim 1 wherein the primary filter and the secondary filter have the same cross section as the housing.

5. The device as recited in claim 1 wherein the secondary filter comprises a first mesh substrate, a second mesh substrate situated downstream of the first mesh substrate, and adsorbent resin intermediate the first and second mesh substrates.

6. The device as recited in claim 1 wherein the heater element, the primary filter and the secondary filter are coaxial to the longitudinal axis of the housing.

7. The device as recited in claim 1 wherein the heater element, the primary filter and the secondary filter are in fluid communication with each other.

8. The device as recited in claim 1 further comprising a means for preventing thermal conductance from the heater element to the secondary filter.

9. The device as recited in claim 1 wherein the secondary filter reversibly sequesters vapor phase and solid phase compounds.

10. The device as recited in claim 1 further comprising a separator disposed between the primary filter and the secondary filter.

11. The device as recited in claim 1 wherein the primary filter and the secondary filter are simultaneously removably received by the housing.

12. The device as recited in claim 1 wherein the secondary filter simultaneously collects the vaporized particles from the primary fitter and gaseous moieties that pass through the primary filter, and wherein pressure is provided from the primary filter to the secondary filter when the heating element is activated.

13. A device, comprising:
- a housing having a proximal end adapted to receive a negative pressure gradient and a distal end adapted to receive solid and gaseous phase moieties for sampling;
- a heating element spaced from the distal end and positioned within the housing;
- a primary filter located downstream from the heating element and encased by the housing, said primary lifter is adapted to capture the solid moieties and said heating element is adapted to vaporize the solid moieties to form vaporized moieties therefrom; and
- a secondary filter located downstream from the heating element and the primary filter, said secondary filter is adapted to capture the gaseous phase moieties which pass through the primary falter and the vaporized moieties from the primary filter, said secondary filter removably received by the housing;
- wherein when the heating element is activated, negative pressure is provided downstream through the housing and from the primary filter to the secondary filter.

* * * * *